(12) United States Patent
Orii et al.

(10) Patent No.: US 8,698,076 B2
(45) Date of Patent: Apr. 15, 2014

(54) DIFFERENTIAL MOBILITY ANALYZER, PARTICLE MEASURING SYSTEM, AND PARTICLE SORTING SYSTEM

(75) Inventors: Takaaki Orii, Wako (JP); Satoshi Kudoh, Wako (JP)

(73) Assignee: Riken, Wako-shi (JP)

( * ) Notice: Subject to any disclaimer, the term of this patent is extended or adjusted under 35 U.S.C. 154(b) by 70 days.

(21) Appl. No.: 12/979,415

(22) Filed: Dec. 28, 2010

(65) Prior Publication Data
US 2012/0001067 A1 Jan. 5, 2012

(30) Foreign Application Priority Data

Feb. 2, 2010 (JP) .................................. 2010-021552

(51) Int. Cl.
*H01J 49/48* (2006.01)

(52) U.S. Cl.
USPC .......................................... 250/294; 250/288

(58) Field of Classification Search
USPC .................................. 250/281–283, 288, 294
See application file for complete search history.

(56) References Cited

U.S. PATENT DOCUMENTS

| | | | |
|---|---|---|---|
| 5,592,096 A | 1/1997 | Pourprix | |
| 5,620,100 A | 4/1997 | Pourprix | |
| 5,621,208 A | 4/1997 | Pourprix | |
| 5,869,831 A * | 2/1999 | De La Mora et al. | 250/288 |
| 5,936,242 A * | 8/1999 | De La Mora et al. | 250/288 |
| 6,012,343 A | 1/2000 | Boulaud | |

(Continued)

FOREIGN PATENT DOCUMENTS

| | | |
|---|---|---|
| JP | 7318477 | 12/1995 |
| JP | 7323240 | 12/1995 |

(Continued)

OTHER PUBLICATIONS

Knutson et al., "Aerosol Classification by Electric Mobility: Apparatus, Theory, and Applications", J. Aerosol Sci., 1975, vol. 6, pp. 443-451.

(Continued)

*Primary Examiner* — David A Vanore
*Assistant Examiner* — Wyatt Stoffa
(74) *Attorney, Agent, or Firm* — Brundidge & Stanger, P.C.

(57) ABSTRACT

In order to provide a differential mobility analyzer and the like that allows (i) easy increase of an upper limit of particle size of charged particle which can be classified and (ii) analysis of charged particles whose particle size is variable, a DMA (Differential Mobility Analyzer) includes: a classification tank in which an inlet electrode having an inlet slit, an intermediate electrode having a slit, and an outlet electrode having an outlet slit are arranged in sequence in such a manner that adjacent electrodes are disposed opposing each other at predetermined intervals; a gas supply section supplying the classification tank with sheath gas; and a voltage generator applying a predetermined voltage between the electrodes disposed opposing each other, the classification tank including a first classification section and a second classification section each formed by the electrodes disposed opposing each other, and the gas supply section controlling a flow rate of the sheath gas to be supplied to the classification tank individually per first classification section and second classification section.

13 Claims, 9 Drawing Sheets

(56) References Cited

U.S. PATENT DOCUMENTS

| | | | |
|---|---|---|---|
| 6,230,572 B1 | 5/2001 | Pui | |
| 6,374,194 B1 | 4/2002 | Takeuchi | |
| 7,521,673 B2 * | 4/2009 | Arcas et al. | 250/294 |
| 7,855,360 B2 * | 12/2010 | Fernandez de la Mora et al. | 250/294 |
| 7,928,374 B2 * | 4/2011 | Rus-Perez et al. | 250/292 |
| 2001/0031564 A1 | 10/2001 | Suzuki | |
| 2004/0045341 A1 | 3/2004 | Suzuki | |
| 2007/0044580 A1 * | 3/2007 | Arcas et al. | 73/865.5 |
| 2008/0017795 A1 * | 1/2008 | Ramiro Arcas et al. | 250/294 |
| 2008/0121794 A1 * | 5/2008 | Miller et al. | 250/294 |
| 2008/0203290 A1 * | 8/2008 | Fernandez de la Mora et al. | 250/281 |
| 2008/0251714 A1 * | 10/2008 | Juan et al. | 250/288 |
| 2010/0096547 A1 * | 4/2010 | Allmaier et al. | 250/294 |

FOREIGN PATENT DOCUMENTS

| | | |
|---|---|---|
| JP | 10-288600 | 10/1998 |
| JP | 11-264790 | 9/1999 |
| JP | 11-297582 | 10/1999 |
| JP | 2001133387 | 5/2001 |
| JP | 2001-239181 | 9/2001 |
| JP | 2001276661 | 10/2001 |
| JP | 2006308370 | 11/2006 |
| JP | 2007-064893 | 3/2007 |

OTHER PUBLICATIONS

Rader, et al., "Application of the Tandem Differential Mobility Analyzer to Studies of Droplet Growth or Evaporation", J. Aerosol Sci., vol. 17, No. 5, pp. 771-787, 1986.

Santos, et al., "Performance Evaluation of a High-Resolution Parallel-Plate Differential Mobility Analyzer" Atmos. Chem. Phys., 9, 2419-2429.

Li, et al., "Performance of Nano-DMA Operated With Different Gases for Sheath and Aerosol Carrier Flows", Aerosol Science and Technology, 39:919-928, 2005.

"A Novel Multi-Layer Differential Mobility Analyzer" A Collection of Papers Presented at the $27^{th}$ Symposium on Aerosol Science and Technology, pp. 195-196 Published on Aug. 3, 2010.

"Development of a Novel Double-Layer Differential Mobility Analyzer", A Collection of Papers Presented at the $27^{th}$ Symposium on Aerosol Science and Technology pp. 263-264 Published on Aug. 3, 2010.

"Development of a Novel Double-Layer Differential Mobility Analyzer (DLDMA)", International Aerosol Conference 2010 (Organized by International Aerosol Research Assembly and Finnish Association for Aerosol Research (FAAR).

\* cited by examiner

DIFFERENTIAL MOBILITY ANALYZER, PARTICLE MEASURING SYSTEM, AND PARTICLE SORTING SYSTEM

This Nonprovisional application claims priority under 35 U.S.C. §119(a) on Patent Application No. 2010-021552 filed in Japan on Feb. 2, 2010, the entire contents of which are hereby incorporated by reference.

TECHNICAL FIELD

The present invention relates to a differential mobility analyzer, a particle measuring system including the differential mobility analyzer, and a particle sorting system including the differential mobility analyzer.

BACKGROUND ART

In recent years, fine particles such as dust and mist suspended in gaseous atmosphere have been receiving attention, in association with suppression of particle contamination in a semiconductor manufacturing process, development of quantum nanoscale material, clarification of generating mechanism of acid rain and smog in the air, and so on.

Differential mobility analyzers (DMAs) have been used to classify aerosol particles that are of nanometer-scale to micrometer-scale particle size. The DMAs make use of a phenomenon that electrical mobility of charged particles in airflow is dependent on their particle size. Cylindrical differential mobility analyzers (CDMAs) are widely used among the DMAs (see Non Patent Literature 1). As a result of significant progress in the recent years, the DMAs are now capable of classifying charged particles having such minimal particle size as 10 nanometers or less at the smallest, and are operable even under reduced pressure (see Patent Literature 1).

FIG. 9 illustrates an example of a conventional CDMA. As illustrated in FIG. 9, a CDMA 800 has a double cylinder structure including a central rod (inner cylinder) 1 and a surrounding body (outer cylinder) 2. A predetermined voltage is applied between an inner peripheral surface of the surrounding body 2 (outer cylinder electrode) and an outer peripheral surface of the central rod 1 (inner cylinder electrode) by a variable voltage generator. Sheath gas is supplied from a supply opening (not illustrated) provided above the surrounding body 2 so as to form a laminar flow in a space between the surrounding body 2 and the central rod 1. The surrounding body 2 has an annular inlet slit 3 in its upper part, from which the charged particles are introduced into the analyzer. The central rod 1 has an annular outlet slit 4 in its lower part, from which the charged particles having been classified are discharged outside the analyzer.

The following description deals with a principle of classifying particles in the CDMA 800. Assume that, in the CDMA 800, a laminar flow condition of the sheath gas is not effected by sample gas containing the charged particles while the sample gas containing the charged particles is introduced via the inlet slit 3 at a predetermined flow rate Qa and discharged from the outlet slit 4 at the same flow rate Qa with respect to a sufficient flow rate of the sheath gas. The charged aerosol particles (charged particles), once entered via the inlet slit 3 into the analyzer, travels downwards in a central axis direction along the inner wall of the surrounding body 2, together with the sheath gas forming the laminar flow in the space between the surrounding body 2 and the central rod 1. Meanwhile, due to an effect caused by an electric field (electrostatic attraction) generated by the variable voltage generator between the surrounding body 2 and the central rod 1, just the aerosol particles of one polarity are attracted toward the central rod 1 at velocities corresponding to their electrical mobility. The electrical mobility is dependent on the particle size of each particle. On this account, just the aerosol particles having a particular particle size reach the outlet slit 4 and are discharged outside the analyzer via the outlet slit 4.

The electrical mobility Zp of the charged particle is calculated by the following equation (1):

$$Zp = Qs \cdot \ln(R2/R1)/(2 \cdot \pi \cdot V \cdot L) \qquad (1)$$

In the equation (1), Qs is a flow rate of the sheath gas, R2 is a radius of the surrounding body 2, and R1 is a radius of the central rod 1, as illustrated in FIG. 9. L is a distance between the inlet slit 3 and the outlet slit 4 along a direction parallel to the central axis. V is the voltage applied between the inner peripheral surface of the surrounding body 2 and the outer peripheral surface of the central rod 1.

The electrical mobility Zp of the charged particle can also be calculated by the following equation (2):

$$Zp = q \cdot e \cdot Cc/(3 \cdot \pi \cdot \mu \cdot Dp) \qquad (2)$$

In the equation (2), q is a charge amount of the charged particle, e is an elementary electric charge, Cc is a Cunningham correction factor, $\mu$ is a coefficient of viscosity of the sheath gas, and Dp is a particle diameter of the charged particle.

By solving the equations (1) and (2) simultaneously, the following equation (3) is achieved:

$$Dp = (2 \cdot V \cdot L \cdot q \cdot e \cdot Cc)/(3 \cdot \mu \cdot Qs \cdot \ln(R2/R1)) \qquad (3)$$

It is understood from the equation (3) that the particle diameter Dp of the charged particle to be classified is calculated as a function of the applied voltage V.

CITATION LIST

Patent Literature 1

Japanese Patent Application Publication Tokukaihei No. 11-264790 A (1999) (Publication Date: Sep. 28, 1999)

Patent Literature 2

Japanese Patent Application Publication Tokukaihei No. 10-288600 A (1998) (Publication Date: Oct. 27, 1998)

Patent Literature 3

U.S. Pat. No. 7,521,673 B2 (Issue Date: Apr. 21, 2009)

Non Patent Literature 1

E. O. Knutson and K. T. Whitby, J. Aerosol Sci., 6, pp. 443 to 451, 1975

Non Patent Literature 2

D. J. Rader and P. H. McMurry, J. Aerosol Scl., 17, pp. 771 to 787, 1986

Non Patent Literature 3

J. P. Santos et al., Atmos. Chem. Phys., 9, pp. 2419 to 2429, 2009

SUMMARY OF INVENTION

Technical Problem

A first problem of the conventional DMAs is that it is not easy to increase an upper limit of the particle size of the charged particles that can be classified.

For example, as apparent from the above-mentioned equation (3), a possible technique for increasing the upper limit of the particle size of the charged particles that can be classified by the DMA is to apply a larger voltage V between the electrodes. However, application of a large voltage results in a dielectric breakdown between the electrodes. That is, there is a problem that the upper limit of the applied voltage V is bounded by a voltage Vmax at which the dielectric breakdown occurs.

Alternatively, various attempts have been made to extend the distance L between the inlet slit and the outlet slit, in order to increase the upper limit of the particle size of the charged particles that can be classified. For instance, Patent Literature 2 discloses a DMA that allows a classification range to be continuously changed. The DMA of Patent Literature 2 includes (i) a surrounding body connected movably to a base section via an elastic member and (ii) central rod connected to the base section and extending toward the inside of the surrounding body. Since the base section and the surrounding body are connected movably, it is possible to continuously change a distance between an inlet slit provided in the surrounding body and an outlet slit provided in the central rod by moving the surrounding body up and down, while maintaining the surrounding body in a sealed state.

However, changing the distance L by the foregoing techniques is structurally complicated and difficult to accomplish. Furthermore, a change in the distance L denotes a change in the position of at least one of the inlet slit and the outlet slit. This requires moving positions of other devices (a charging device, a particle collection device, and the like) that are connected to the DMA so that the devices are followed by the DMA or that the devices follow the DMA. If these other devices are not to be moved, additional flow paths are necessarily provided between the inlet slit or outlet slit and the other devices. In a case where the additional flow paths are provided, diffusional deposition of the aerosol particles on a tube wall of the flow paths is increased. In particular, the aerosol particle having a small particle size is more likely to be effected by a decrease in transport efficiency due to diffusion deposition or the like, which transport efficiency is dependent on the particle size. As a consequence, a problem arises that an accurate particle size distribution cannot be obtained unless the effect of the diffusional deposition and the like is compensated.

A second problem of the conventional DMAs is that it is difficult to analyze charged particles whose particle size may change in the process of classification. An example of such particles is volatile aerosol particles.

The DMAs often use dry air and clean gas such as pure nitrogen, as the sheath gas. Generally, the sheath gas and sample gas have different component compositions. Furthermore, the aerosol particles (volatile aerosol particles) composed of material m with a relatively high vapor pressure maintain their particle size by being kept in an equilibrium state with gaseous material m at its saturated vapor pressure contained in the sample gas. As such, in a case where the volatile aerosol particles are classified by use of the DMA, it is generally inevitable that the volatile aerosol particles are reduced in particle size due to evaporation into the sheath gas. Especially if the components of the aerosol particles whose particle diameters are to be measured are unknown, the vapor pressure of the aerosol particles is often unknown as well. Classification using the DMA thus has a problem that it is not possible to determine whether the particle size of the aerosol particles has changed, let alone how much the particle size has changed.

Non Patent Literature 2 discloses a method for assuming how much the volatile aerosol particles evaporate in the DMA, by use of a tandem DMA measurement system in which two DMAs are serially connected. In such a DMA, however, the aerosol particles remain for a relatively long time in the connecting section connecting the two DMAs. This causes a problem that accuracy of the results cannot be expected, especially in a case where a material with a relatively high volatility is used.

Moreover, parallel plate DMAs using plate electrodes have come into use lately (see Patent Literature 3 and Non Patent Literature 3). For example, in a DMA illustrated in FIG. 3 of Patent Literature 3, a plurality of plate electrodes provided with respective slits through which particles pass are arranged parallel to each other. Patent Literature 3 discloses that dispersion of the particles to be collected is relatively reduced by having the particles pass through plurality of particle passing slits. However, the foregoing two problems remain unsolved.

The present invention is achieved in view of the above-described situation, and an object of the present inventions is to provide a differential mobility analyzer and the like that can (i) easily increase an upper limit of particle size of charged particles that can be classified and (ii) analyze the charged particles whose particle size is variable.

Solution to Problem

In order to attain the above object, a differential mobility analyzer (DMA) according to the present invention includes: a classification tank including n (where n is an integer equal to or greater than 3) pieces of electrodes each having a planar shape, disposed in sequence in such a manner that the electrodes oppose each other as pairs each having a predetermined space provided therebetween, each of the n pieces of electrodes having at least one slit through which the charged particles pass; a gas supply section supplying the classification tank with sheath gas; and a voltage supply section applying a predetermined voltage between each of the pairs of the electrodes disposed opposing each other in the classification tank, the classification tank including (n−1) stages of classification sections for classifying the charged particles, each of the classification sections being formed by a respective one of the pairs of the electrodes disposed opposing each other, and the gas supply section controlling a flow rate of the sheath gas supplied to the classification tank per classification section.

With the above configuration, the flow rate of the sheath gas is individually controllable per classification section. As such, it is possible to relatively easily change an analysis condition by units of classification sections without substantially changing the configuration of the classification tank. This allows, for example, increasing the upper limit of the particle size of the charged particles that can be classified. In addition, multistage classification efficiently eliminates gas components from the sample gas containing the charged particles so that particles having a particular particle size are collected with a higher purity.

The present invention further provides a particle measuring system including: the foregoing differential mobility analyzer; and a particle component measuring device analyzing chemical component of particles classified by the differential mobility analyzer.

The present invention further provides a particle sorting system including: the foregoing differential mobility analyzer; and a particle sorting device sorting and collecting particles that have a predetermined particle size, the particles being classified by the differential mobility analyzer.

Advantageous Effects of Invention

The present invention makes it possible to provide a differential mobility analyzer and the like which can (i) easily increase the upper limit of particle size of charged particles that can be classified by the differential mobility analyzer, i.e., easily optimize, depending on the particles to be classified, the upper limit of particle size of charged particles that can be classified by the differential mobility analyzer, for example, and (ii) analyze charged particles with a variable particle size.

DESCRIPTION OF EMBODIMENTS

Embodiment 1

Figure 1:
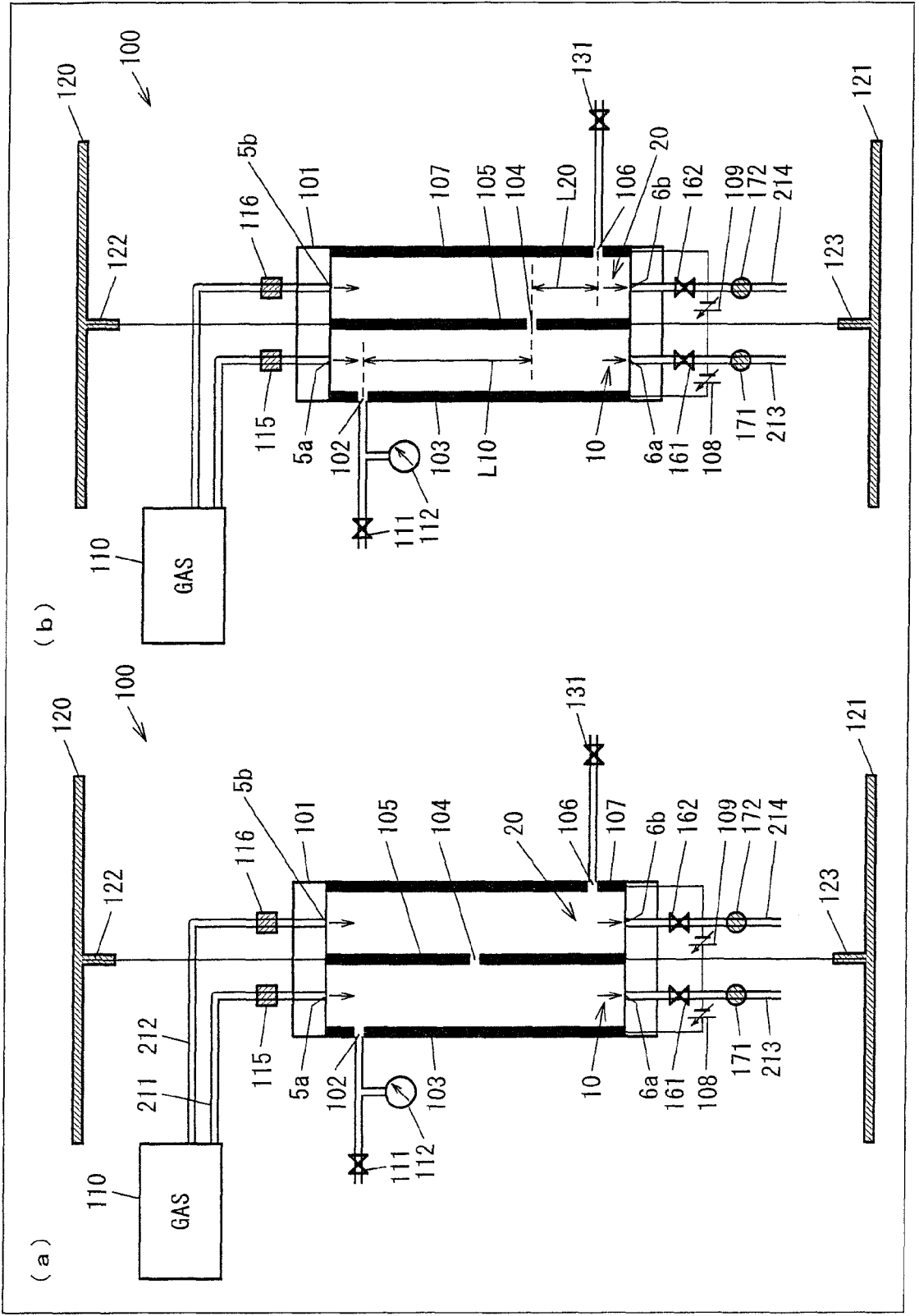
FIGS. 1(a) and (b) are cross-sectional views schematically illustrating configurations of a DMA according to an embodiment of the present invention.
Figure 2:
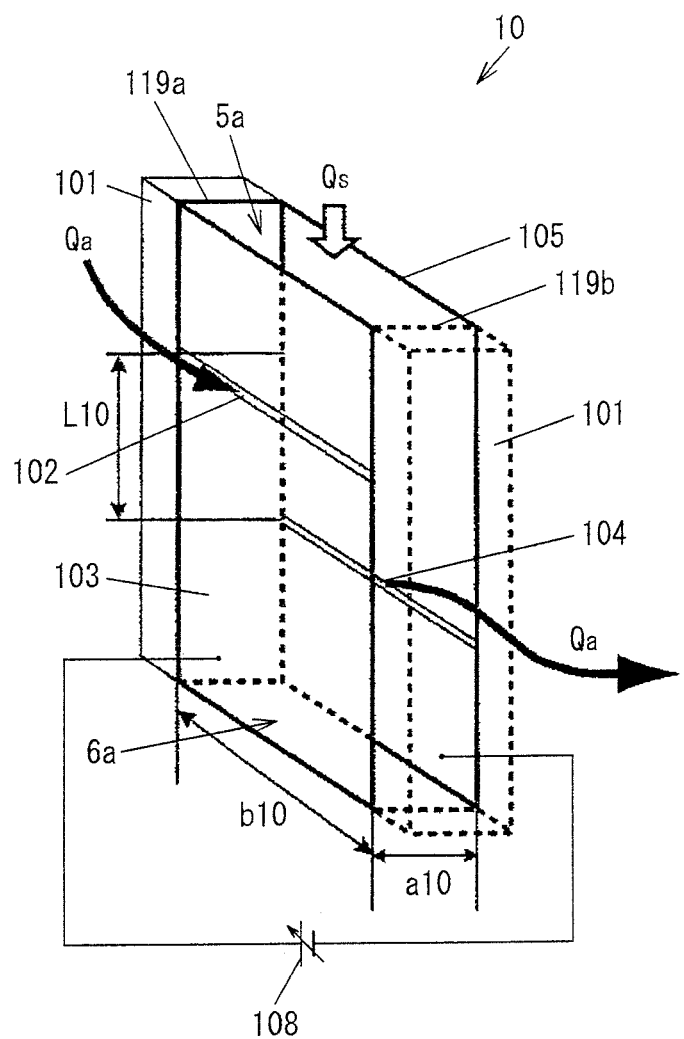
FIG. 2 is a perspective view schematically illustrating a configuration of a classification section included in the DMA illustrated in FIG. 1.

The following describes an embodiment of a DMA according to the present invention with reference to FIGS. 1 and 2.

(Configuration of DMA 100)

With reference to FIG. 1, first described is a general configuration of a DMA 100 according to the present invention. FIG. 1 schematically illustrates cross sections of the DMA 100 taken along a plane perpendicular to slits (to be described).

As illustrated in (a) and (b) of FIG. 1, the DMA 100 according to the present embodiment is, roughly summarized, a device that classifies electrically charged particles (charged particles) in accordance with their electrical mobility. The DMA 100 includes a classification tank 101, a sheath gas supply device 110, and voltage generators 108 and 109.

The classification tank 101 is an insulative housing having a cuboid shape. The classification tank 101 includes an inlet electrode 103, an intermediate electrode 105, and an outlet electrode 107 (three electrodes) arranged parallel to each other in this order, having predetermined spaces provided between each of the electrodes. The inlet electrode 103, the intermediate electrode 105, and the outlet electrode 107 are all identical in shape, i.e., are all rectangular planar electrodes, except for the slits which are provided in different positions, respectively. The inlet electrode 103 and the outlet electrode 107 are respectively formed on inner walls of the classification tank 101 in positions opposing each other. The intermediate electrode 105 is provided between the inlet electrode 103 and the outlet electrode 107 so as to oppose these electrodes, and bisects an inner space of the classification tank 101.

The classification tank 101 includes 2 (=3−1) stages of classification sections for classifying charged particles. Each classification section is formed by an opposing pair of electrodes. That is, the inlet electrode 103, the intermediate electrode 105 opposing the inlet electrode 103, and the inner walls of the housing, i.e., classification tank 101 (which inner walls correspond to wall sections 119a and 119b in FIG. 2) make up a first classification section 10. Further, the intermediate electrode 105, the outlet electrode 107 opposing the intermediate electrode 105, and the inner walls of the classification tank 101 make up a second classification section 20.

Each of the first classification section 10 and the second classification section 20 is a sealed classification space having a pair of slits (to be described) through which the charged particles pass. Each of the first classification section 10 and the second classification section 20 have an inlet slit and outlet slit; the inlet slit is provided in an upstream side of the classification sections in a direction (flow direction) in which the sheath gas flows, and the outlet slit is provided in a downstream side of the classification sections in the flow direction. Further, in the DMA 100, adjacent classification sections (the first classification section 10 and the second classification section 20) share the intermediate electrode 105 and the slit 104 provided in the intermediate electrode 105.

The first classification section 10 is a classification section of an upstream stage with respect to the second classification section 20. Sample gas containing charged aerosol particles (charged particles) is introduced into the first classification section 10 through an inlet slit (slit) 102 opened in the inlet electrode 103 which forms the first classification section 10. Part of the charged aerosol particles introduced into the first classification section 10 is introduced into the second classification section 20 of a downstream stage through the slit 104 located on the downstream side in the direction in which the sheath gas flows. Subsequently, part of the charged aerosol particles introduced into the second classification section 20 is discharged outside the second classification section 20 (outside the classification tank 101) through an outlet slit 106 located on the downstream side in the direction in which the sheath gas flows. In other words, the slit 104 opened in the intermediate electrode 105 serves as an outlet slit of the first classification section 10 and an inlet slit of the second classification section 20.

The inlet slit 102, the slit 104, and the outlet slit 106 are openings that are open in a direction perpendicular to the vertical direction (direction in which the sheath gas flows) and are provided parallel to each other.

The sheath gas supply device 110 supplies clean gas such as clean nitrogen gas or clean air to the classification tank 101, as the sheath gas. Note that the clean gas flowed through the classification tank 101 and thereafter discharged may be collected for cyclic use (recycling). In this case, the sheath gas supply device 110 filters the collected clean gas for purification.

The sheath gas supply device 110 and the classification tank 101 are connected to each other via gas supply pipes 211 and 212. More specifically, the gas supply pipe 211 connects the sheath gas supply device 110 and a sheath gas inlet 5a so as to supply the clean gas into the first classification section 10 as the sheath gas. The gas supply pipe 212 connects the sheath gas supply device 110 and a sheath gas inlet 5b so as to supply the clean gas into the second classification section 20 as the sheath gas. The gas supply pipe 211 has a massflow controller (MFC: gas supply control means) 115. The gas supply pipe 212 has a massflow controller (MFC: gas supply control means) 116.

Each of the MFCs 115 and 116 measures mass of the sheath gas respectively supplied to the first classification section 10 and the second classification section 20, and automatically controls supply flow rate of the sheath gas to the classification sections based on the measurement results. In other words, the DMA 100 is configured so that the flow rate of the sheath gas supplied to the first classification section 10 and the second classification section 20 are individually controllable by use of the MFCs 115 and 116. In the DMA 100, a gas supply section is made up of the sheath gas supply device 110, the gas supply pipes 211 and 212, and the MFCs 115 and 116.

The sheath gas that has flown through the classification tank 101 is discharged outside the classification tank 101 via gas discharge pipes 213 and 214. The gas discharge pipe 213 connects the sheath gas outlet 6a at the bottom of the first classification section 10 to a discharge pump (not illustrated). The gas discharge pipe 213 is provided with a flow rate adjusting valve 161 and a massflow meter (MFM) 171, which arbitrarily control the discharge amount of the sheath gas. The gas discharge pipe 214 connects the sheath gas outlet 6b at the bottom of the second classification section 20 to a discharge pump (not illustrated). The gas discharge pipe 214 is provided with a flow rate adjusting valve 162 and a massflow meter (MFM) 172, which arbitrarily control the discharge amount of the sheath gas.

In a classification operation using the DMA 100, first, all the valves leading to the outside of the classification tank 101 (i.e., on-off valves 111 and 131, the flow rate adjusting valves 161 and 162, and the massflow controllers 115 and 116) are closed so that the classification section 101 is made to be a closed system. Then, the flow rate adjusting valves 161 and 162 and the massflow controllers 115 and 116 are controlled so that, in each classification section, the supply flow rate and the discharge flow rate of the sheath gas equal out and thus a laminar flow is formed. A pressure gauge 112 monitors pressure within the classification tank 101, and adjusts the supply flow rate and the discharge flow rate of the sheath gas so that the pressure in the classification tank is maintained at a target level (for example, at an environmental pressure of the sample gas). Subsequently, the on-off valves 111 and 131 are opened so that the sample gas is introduced into the DMA 100, and classification of the sample gas is performed. That is, in the DMA 100, as a result of the above-described control, the supply flow rate and the discharge flow rate of the sheath gas substantially equal out in each classification section. This allows formation of the laminar flow of the sheath gas in each classification section, while also realizing a state in which there is substantially no pressure difference between the classification sections.

The voltage generator (voltage supply section) 108 applies a predetermined voltage between the inlet electrode 103 and the intermediate electrode 105, which electrodes configure the first classification section 10. The voltage generator (voltage supply section) 109 applies a predetermined voltage between the intermediate electrode 105 and the outlet electrode 107, which electrodes configure the second classification section 20. The voltage generators 108 and 109 are variable voltage generators that can change the voltage to be applied to a desired value. That is, the DMA 100 is configured so that the voltages applied to the respective classification sections (the first classification section 10 and the second classification section 20) are independently controllable.

Above and below the classification tank 101 are provided position adjusting mechanisms 120 and 121 that adjust the position of the intermediate electrode 105. The position adjusting mechanisms 120 and 121 are provided with respective guide rails 122 and 123 extended in the vertical direction to the intermediate electrode 105. The intermediate electrode 105 are continuously movable in an up-and-down direction (in the direction in which the sheath gas flows and its counter direction) along the guide rails 122 and 123 and is fixable at a desired position. At the same time, the position of the slit 104 in the intermediate electrode 105 is also continuously movable in the up-and-down direction. That is, in the DMA 100, moving the intermediate electrode 105 up and down allows changing a relative position of a pair of slits in the first classification section 10 and the relative position of a pair of slits in the second classification section 20.

For example, (b) of FIG. 1 depicts a state where the slit 104 is positioned lower with respect to (a) of FIG. 1 due to movement of the intermediate electrode 105 along the guide rails 122 and 123. In comparison with (a) of FIG. 1, the state illustrated in (b) of FIG. 1 has a longer classification length L10 in the first classification section 10 and a shorter classification length L20 in the second classification section 20.

(Operation Principle of DMA 100)

With reference to FIGS. 1 and 2, an operation principle of the DMA 100 is now described. Note that the operation principle of the classification is common to all classification sections, irrespective of how many classification sections the DMA 100 includes. On this account, the following description focuses on the operation principle in the first classification section 10.

FIG. 2 is a perspective view schematically illustrating a configuration of a classification section (first classification section 10) included in the DMA 100. Sample gas containing aerosol particles is electrically charged by a charging device (not illustrated) so as to serve as sample gas containing charged aerosol particles. The sample gas is introduced into the classification tank 101 via the inlet slit 102 and led into the first classification section 10. In the first classification section 10, a sufficient flow rate of sheath gas flows via the sheath gas inlet 5a toward the sheath gas outlet 6a, thereby forming a downward laminar flow. Note that, a laminar flow condition of the sheath gas is not effected by the aerosol particles, from the introduction of the aerosol particles via the inlet slit 102 into the first classification section 10 to the discharge from the first classification section 10 via the slit 104.

In the embodiment, a distance between the inlet electrode 103 and the intermediate electrode 105 is a10, lengths of the inlet slit 102 and the slit 104 are b10, a voltage applied between the inlet electrode 103 and the intermediated electrode 105 is V10, and a distance between the inlet slit 102 and the slit 104 along the direction in which the sheath gas flows is L10 (see FIG. 2).

The sample gas introduced into the first classification section 10 is flown downstream along the inner wall of the inlet electrode 103 according to the laminar flow of the sheath gas. Once the voltage V10 is applied between the inlet electrode 103 and the intermediate electrode 105, the charged aerosol particles of one polarity travel from the inlet electrode 103 toward the intermediate electrode 105 due to an electrostatic attraction. The electrical mobility Zp of the charged aerosol particle at this time is represented by the following equation (4):

$$Zp = Qs10 \cdot a10/(b10 \cdot V10 \cdot L10) \qquad (4)$$

In the equation (4), Qs10 is a flow rate of the sheath gas; and a10, b10, V10, and L10 are as described above.

The electrical mobility Zp of the charged aerosol particle can also be calculated by the following equation (5):

$$Zp = q \cdot e \cdot Cc/(3 \cdot \pi \cdot \mu \cdot Dp) \qquad (5)$$

In the equation (5), q is a charge amount of the charged particle, e is an elementary electric charge, Cc is a Cunningham correction factor, µ is a coefficient of viscosity of the sheath gas, and Dp is a particle diameter of the charged aerosol particle.

In the embodiment, just the charged aerosol particles having the particle diameter Dp calculated by simultaneously solving the equations (4) and (5) pass through the slit 104 and are introduced into the subsequent second classification section 20.

Further, the following equation is satisfied also in the second classification section 20.

$$Zp = Qs20 \cdot a20/(b20 \cdot V20 \cdot L20) \qquad (6)$$

Just the particles having the particle diameter Dp calculated by simultaneously solving the equations (5) and (6) reach the outlet slit 106 and are discharged outside the DMA 100 via the outlet slit 106. In the equation (6), Qs20 is a flow rate of the sheath gas in the second classification section 20, a20 is a distance between the intermediate electrode 105 and the outlet electrode 107, b20 denotes lengths of the slit 104 and the outlet slit 106, V20 is a voltage applied between the intermediate electrode 105 and the outlet electrode 107, and L20 is a distance between the slit 104 and the outlet slit 106.

(Main Characteristics of DMA 100)

Although not particularly limited, the following are main characteristics of the DMA 100.

(1) Flow Rate of Sheath Gas is Individually Controlled Per Classification Section In the DMA 100, the flow rate of the sheath gas is individually controllable per classification section (the first classification section 10 and the second classification section 20). As shown in the above equation (5), the flow rate of the sheath gas is one factor that determines the classification conditions for a respective classification section. In the DMA 100, the classification conditions can be changed relatively easily per classification section without substantially changing the configuration of the classification tank 101.

For example, with the conventional DMAs, in order to increase the upper limit of the particle diameters of the charged particles that can be classified, the voltage applied to the classification section is made greater. However, this caused a problem that a dielectric breakdown occurs. In the DMA 100, on the other hand, the voltage applied to each classification section is maintained in a level lower than that at which the dielectric breakdown happens, and further the flow rate of the sheath gas in the classification sections is reduced. This makes it possible to increase the upper limit of the particle size of the charged particles that can be classified, relatively easily.

Alternatively, increasing the flow rate of the sheath gas in each classification section allows obtaining sufficient resolution and separation performance of the charged particles from the gas.

It is also possible to use the DMA 100 as a monolayer DMA. This is accomplished by providing no sheath gas to either one of the first classification section 10 and the second classification section 20 and using that classification section as a flow path of the sample gas or the gas containing charged particles that have been classified.

Moreover, because it is relatively easy to change the classification conditions per classification section, the charged particles whose particle size changes in the process of classification can easily be analyzed. The details are described below in (3).

(2) Classification Length is Variable

In the DMA 100, it is possible to change the classification length (a distance between the slits along the direction in which the sheath gas flows) by moving the intermediate electrode 105 in a vertical direction. As shown in the equation (5), the classification length is one factor that determines the classification conditions for a respective classification section. In the DMA 100, the classification conditions can be changed relatively easily per classification section without substantially changing the configuration of the classification tank 101. Therefore, similar effects to those described in the above "(1) Flow rate of sheath gas is individually controlled per classification section" are obtained.

Further, in the DMA 100, the inlet electrode 103 having the inlet slit 102 for introducing the sample gas and the outlet electrode 107 having the outlet slit 106 for discharging the charged particles which have been classified are fixed in position. Just the position of the intermediate electrode 105 sandwiched between the inlet electrode 103 and the outlet electrode 107 can be changed along the direction in which the sheath gas flows. As such, changes in the classification conditions in the respective classification sections do not involve position changes of the inlet slit 102 and the outlet slit 106. Consequently, even if the classification conditions are changed, it is not necessary to move the positions of other devices (the charging device, the particle collection device, and the like) that are provided in a position followed by the DMA 100 and that are provided in a position that follow the DMA 100. Needless to say, no additional flow paths that connect the inlet slit 102 or the outlet slit 106 with the other devices is required. This achieves a further advantage that it is not necessary to consider a change in an extent of a diffusional deposition loss dependent on the particle size of the charged particles.

(3) Efficient Multistage Classification is Possible

The DMA 100 performs a multistage classification using the first classification section 10 and the second classification section 20. The first classification section 10 and the second classification section 20 share the intermediate electrode 105, and the flow path (slit 104) between the two classification sections has a length that can be substantially ignored. Accordingly, a multistage classification can be performed while keeping the effect of the loss due to the diffusion of the charged particles and the like to a minimum degree, upon transporting the gas from one classification section to the subsequent classification section.

Figure 9:
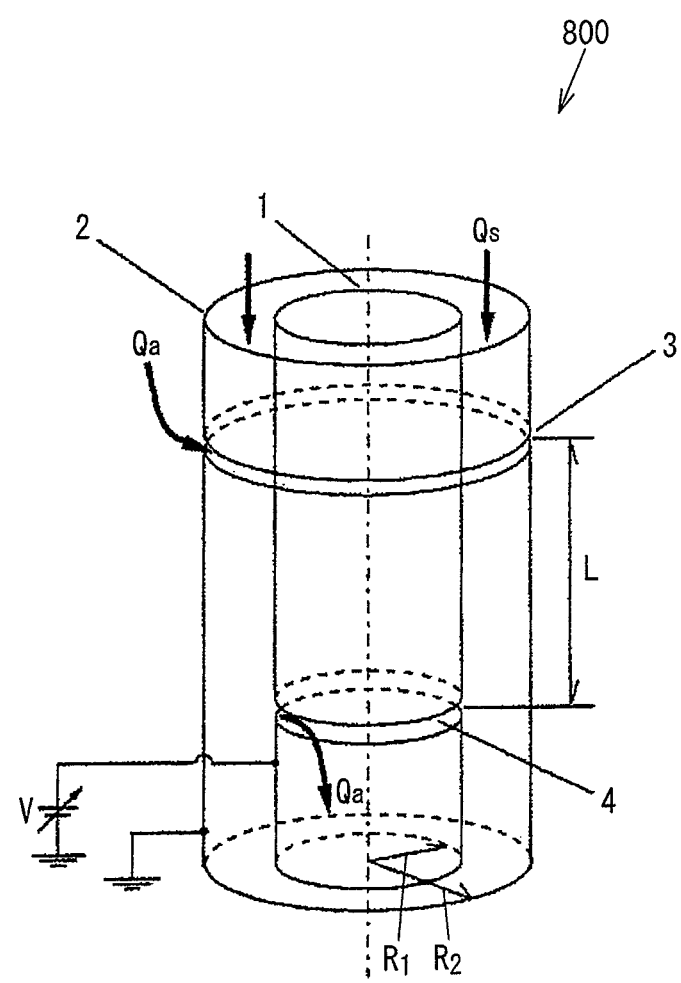
FIG. 9 is a schematic view illustrating a differential mobility analyzer according to a conventional technique.

For example, in the CDMA having such a configuration as illustrated in FIG. 9, it is known that, in an attempt to separate and obtain just the charged particles having a particular particle size, 0.001 to 0.01% or more of coexisting sample gas components are mixed in the separated charged particles (Performance of Nano-DMA Operated with Different Gases for Sheath and Aerosol Carrier Flows: Aerosol Sci. and Tech., 39, pp. 919 to 928 (2005)). On this account, use of the DMA with a conventional structure as a device for sorting the charged particles from gas components of the sample gas (see, e.g., Japanese Patent Application Publication Tokukai No. 2001-239181 A) offers only insufficient gas removal capability. That is, a problem can arise if the charged particles sorted by the conventional DMA are supplied for further use and composition analysis.

The DMA 100, on the other hand, performs a multistage classification to enhance the sample gas removal capability (theoretically, if there are n stages of classification sections (n is an integer equal to or greater than 2), the sample gas removal capability is raised to the power of n). As such, the DMA 100 can collect aerosol particles that have a particular particle size with a higher purity.

(4) Analysis of Change in Particle Size of Charged Particle is Possible

Another advantage of performing the multistage classification is that this allows analyzing changes in particle size of the charged particles during the process of the classification. For example, in a case where the classification conditions in the first classification section 10 and the second classification section 20 are set such that the charged particles having an identical particle size are classified, the charged particles that have not changed in particle size during the classification process are discharged from the outlet slit 106.

On the other hand, in a case where the charged particles are not discharged from the outlet slit 106, it is assumed that the particle size of the charged particles has changed during the classification process. In this case, it is possible to analyze to what extent the particle size of the charged particles is changed by continuously changing the classification condition in the second classification section 20. Such an analysis is especially useful for analyzing volatile charged particles.

The following describes an example of analyzing changes in the particle size of the charged particles by use of the DMA 100. Note that the reference signs used in the following description are the same as in FIG. 1 and as described in the foregoing "(Operation principle of DMA 100)".

In the DMA 100, flow rates of the sheath gas flowing in the first classification section 10 and second classification section 20 are individually controllable. First, in order to allow the charged particles that have a desired particular particle size to pass through the slit 104, calculations are performed based on the equations (4) to (6) under the condition of L10=L20, a10=a20, and b10=b20, thereby setting V10 and Qs10 at optimum values. Next, V10 and Qs10 are set to be V20 and Qs20, respectively (i.e., V20 and Qs20 are set such that the analysis conditions of the classification sections 10 and 20 are the same), and thereafter sample gas containing the charged particles is introduced from the inlet slit 102. Here, the charged particles having the particular particle size, which particles have been classified in the first classification section 10 and have passed through the slit 104, are assumed to be discharged outside the classification tank 101 via the outlet slit 106.

If the charged particles having the desired particle diameter are not discharged from the outlet slit 106, it means that the electrical mobility of the charged particles in the second classification section 20 is different from the electrical mobility of the charged particles in the first classification section 10. On this account, it is deemed that the particle size of the charged particles has changed. In such a situation, based on appropriate Qs10 and Qs20 and fixed V10, V20 is changed continuously or in stages. Subsequently, the V20 at a time when the charged particles are discharged via the outlet slit is recorded, and calculations are performed based on the equations (4) to (6). This makes it possible to calculate the particle size of the charged particles at the time when the charged particles are discharged via the outlet slit 106. In this way, it is possible to know whether or not the charged particles are reduced in their particle size due to evaporation during the process of the classification, or to what extent the particle size is reduced.

Compared to a system in which two conventional CDMAs are connected in tandem, the DMA 100 has substantially no time in which the particles are retained in a flow path connecting DMAs. As such, it is possible to specify just the change in the particle size during the classification process (in the classification tank 101). Moreover, based on a comparison between a particle size distribution in the second classification section 20 and a particle size distribution in the first classification section 10, it is possible to obtain information regarding thermodynamic characteristics of the volatile aerosol particles such as an extent of nucleated growth.

Furthermore, (b) of FIG. 1 allows analyzing particle size of the charged particles even in a case where the charged particles are significantly reduced in size, by increasing the classification length L10 of the first classification section 10 and decreasing the classification length L20 of the second classification section 20. In addition, by optimizing L10 and L20 as well as Qs10 and Qs20, the time for which the charged particles are retained in the classification tank 101 can be optimized to within a predetermined range.

Embodiment 2

Figure 3:
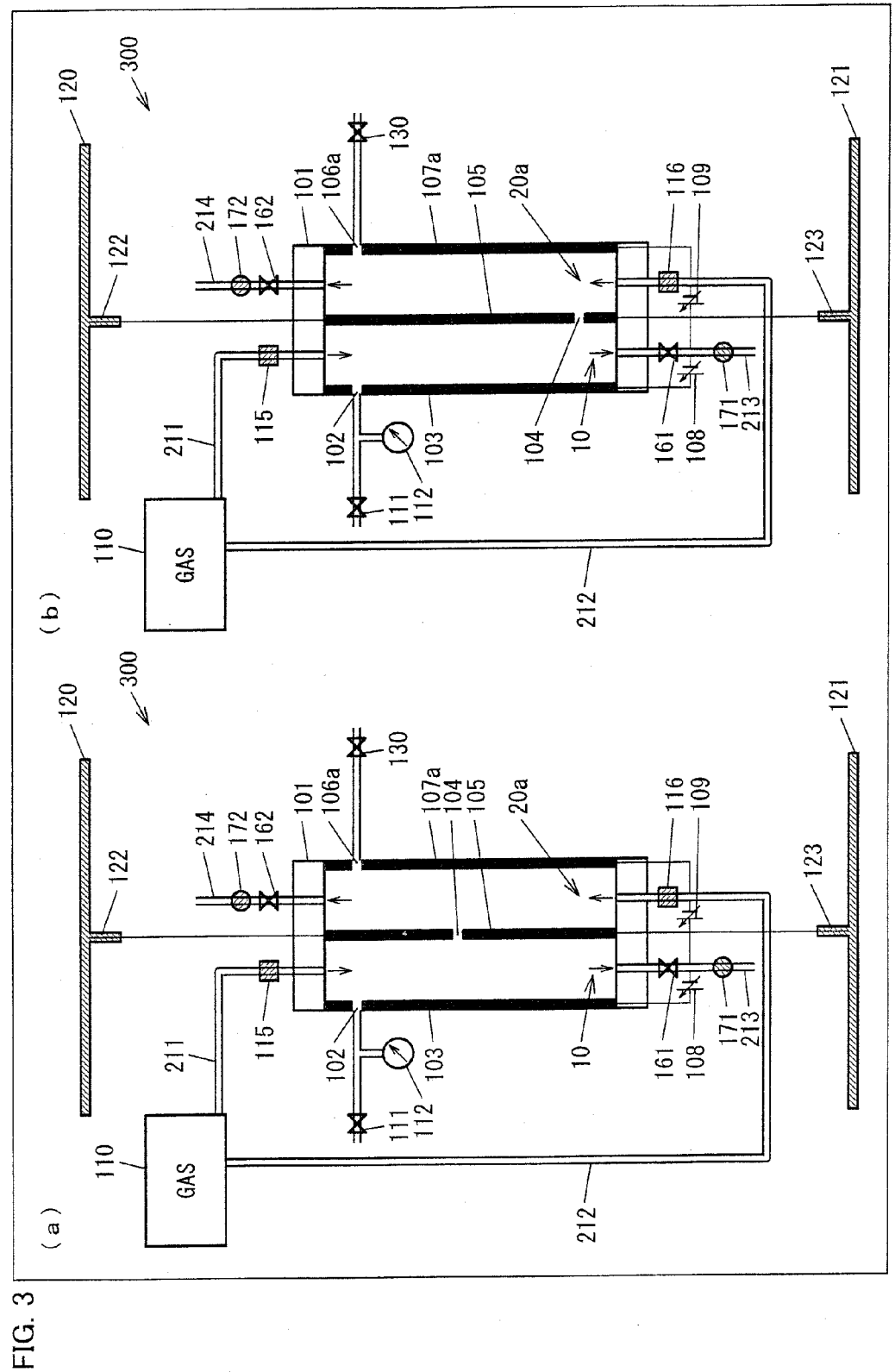
FIGS. 3(a) and (b) are cross-sectional views schematically illustrating configurations of a DMA according to another embodiment of the present invention.

The following describes another embodiment of a DMA according to the present invention with reference to FIG. 3. Schematically illustrated in (a) and (b) of FIG. 3 are cross sections of the DMA 300 taken along a plane perpendicular to the slits. For easy description, members having identical functions as the members in the DMA 100 according to Embodiment 1 are denoted by identical reference signs and are not explained. The present embodiment mainly describes differences from Embodiment 1.

(Configuration of DMA 300)

As illustrated in FIG. 3, the DMA 300 and the DMA 100 according to Embodiment 1 are different just in the configuration of the second classification section and the configurations in the vicinity of the second classification section. Specifically, the DMA 300 includes an outlet electrode 107a instead of the outlet electrode 107 in the DMA 100. The outlet electrode 107a has an outlet slit 106a provided at the same height as the inlet slit 102. The second classification section 20a is made up of the intermediate electrode 105, the outlet electrode 107a opposing the intermediate electrode 105, and the inner walls of the classification tank 101.

In the DMA 300, the first classification section 10 and the second classification section 20 that are adjacent to each other share the intermediate electrode 105 and also the slit 104 opened in the intermediate electrode 105. The slits (inlet slit 102 and the outlet slit 106a) opened in the two electrodes (inlet electrode 103 and the outlet electrode 107a), respectively, which electrodes are disposed opposing the intermediate electrode 105, are positioned at same heights, which is a height higher than the shared slit 104. That is, in the DMA 300, the positional relationship between the slit on the inlet side and the slit on the outlet side in the first classification section is opposite to that in the second classification section. On this account, the directions (flow directions) in which the sheath gas flows in the first classification section 10 and that in the second classification section 20 are necessarily opposite to each other. As such, a gas supply pipe 212 is connected to the bottom of the second classification section 20a and a gas outlet pipe 214 is connected to the top of the second classification section 20a, so that the sheath gas flows from the bottom toward the top.

Note that a configuration similar to the DMA 300 may hereinafter be referred to as a symmetrical DMA, in light of the positional relations of the slits opened in the first classification section 10 and the second classification section that are adjacent to each other. In addition, a configuration similar to the DMA 100 in Embodiment 1 may be referred to as an asymmetrical DMA.

(Operation Example of DMA 300)

In the DMA 300, the sample gas containing the charged particles is introduced into the first classification section 10 via the inlet slit 102. Then, as a result of a classification in the first classification section 10, just the charged particles that have a predetermined particle size are introduced into the second classification section 20a via the slit 104 positioned in a downstream side of the direction in which the sheath gas flows (lower side). Subsequently, as a result of a classification in the second classification section 20a, just the charged particles having a predetermined particle size are discharged outside the classification tank 101 via the outlet slit 106a positioned in a downstream side of the direction in which the sheath gas flows (upper side).

As illustrated in (a) and (b) of FIG. 3, in the DMA 300, the classification length (distance between the slits) in the first classification section 10 is always equal to the classification length in the second classification section 20a, even in a case where the intermediate electrode 105 is moved in a vertical direction.

(Main Characteristics of DMA 300)

Although not particularly limited, the following are main characteristics of the DMA 300 compared with those of the DMA 100 described in Embodiment 1. Note that the DMA 300 shares all the advantages achieved by the DMA 100, and any overlapping descriptions are omitted in the present embodiment.

(1) Wide Range of Multistage Classification is Possible while Maintaining a Compact Device Length For example, assume that, in the DMA 100 illustrated in FIG. 1, a multistage classification is performed in the first classification section 10 and the second classification section 20 under the completely same conditions. In this case, the position of the intermediate electrode 105 is set such that the classification lengths meet the relation of L10=L20 (see (a) of FIG. 1). On this account, the upper limit of the classification lengths that can be secured in the first classification section 10 and the second classification section 20 is about a half of the length of each classification section.

Meanwhile, in the DMA 300, the classification lengths that can be secured in the first classification section 10 and the second classification section 20 are always equal, irrespective of the position of the intermediate electrode 105. As such, even on the assumption that the multistage classification is performed in the first classification section 10 and the second classification section 20a under the completely same classification conditions, it is possible to secure the classification lengths substantially equal to the length of each classification section (see (b) of FIG. 3).

That is, the DMA 300 allows securing greater classification lengths while maintaining the length of the device compact. In consequence, it is possible to perform a multistage classification of the charged particles having a wider range of particle diameters, while maintaining the length of the device compact.

Embodiment 3

Figure 4:
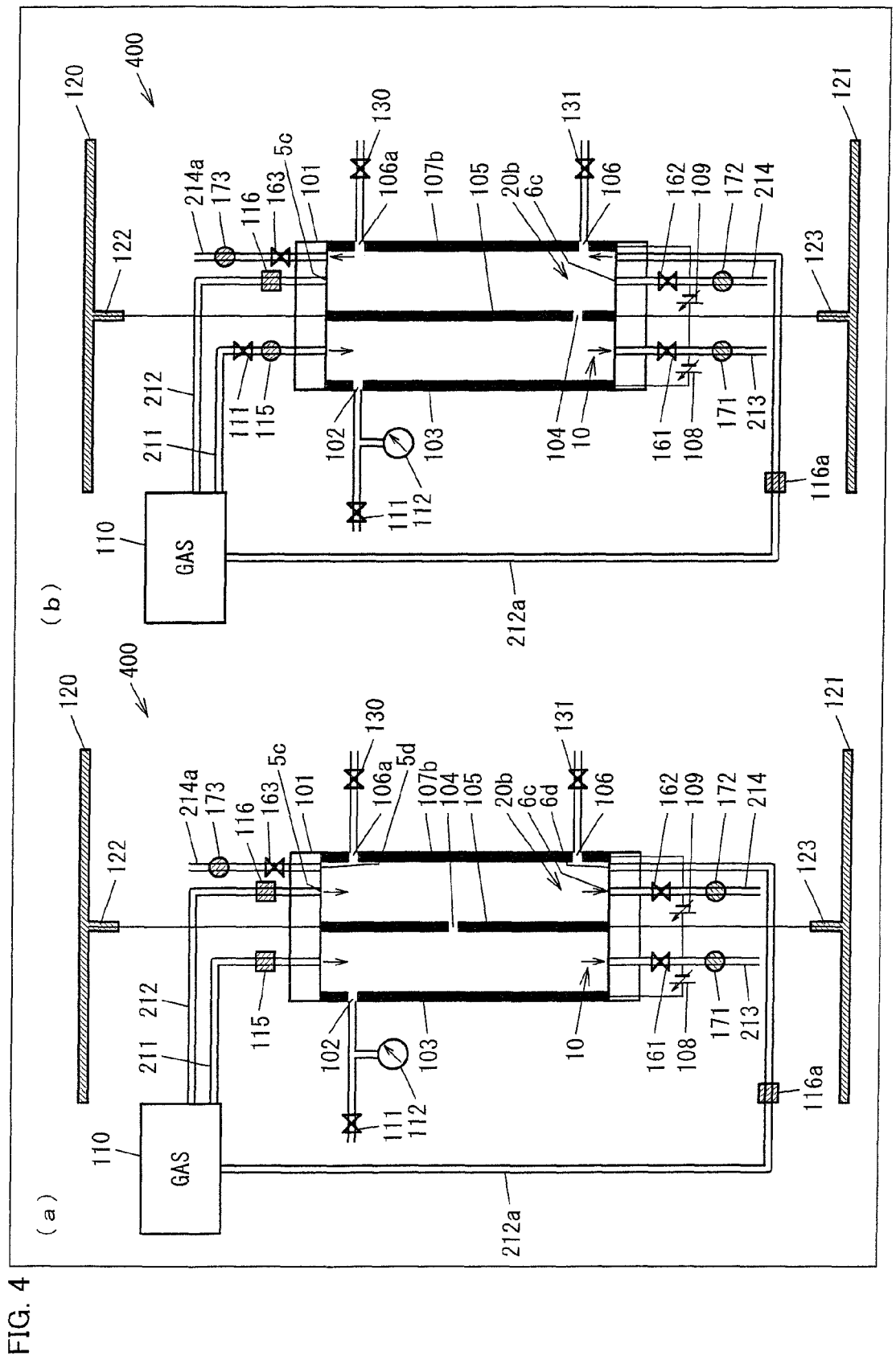
FIGS. 4(a) and (b) are cross-sectional views schematically illustrating configurations of a DMA according to still another embodiment of the present invention.

The following describes still another embodiment of the DMA according to the present invention with reference to FIG. 4. Schematically illustrated in (a) and (b) of FIG. 4 are cross sections of the DMA 400 taken along a plane perpendicular to the slits. For easy explanation, the components having the same functions as the elements of the DMA 100 according to Embodiment 1 are denoted by the same reference signs and are not described. The present embodiment mainly describes differences from Embodiments 1 and 2.

(Configuration of DMA 400)

As illustrated in FIG. 4, the DMA 100 according to Embodiment 1 and the DMA 400 are different just in the configuration of the second classification section and its vicinity configurations. Specifically, the DMA 400 includes, instead of the outlet electrode 107 in the DMA 100, an outlet electrode 107b having two outlet slits 106a and 106 at different heights. The second classification section 20b is made up of the intermediate electrode 105, the outlet electrode 107b opposing the intermediate electrode 105, and the inner walls of the classification tank 101.

The outlet slit 106a is provided at the same height as the inlet slit 102. The outlet slit 106 is provided lower than the outlet slit 106a. A particle discharge pipe connected to the outlet slit 106a is provided with an on-off valve 130, and a particle discharge pipe connected to the outlet slit 106 is provided with an on-off valve 131. When the DMA 400 is in use, one of the on-off valves 130 and 131 is opened and the other is closed. This allows to selectively use one of the outlet slits 106a and 106.

An opening 5c located at the top of the second classification section 20b is connected to the sheath gas supply device 110 via a gas supply pipe 212. An opening 5d located at the top of the second classification section 20b is connected to a gas discharge pipe 214a. An opening 6c located at the bottom of the second classification section 20b is connected to a gas discharge pipe 214. An opening 6d located at the bottom of the second classification section 20b is connected to the sheath gas supply device 110 via a gas supply pipe 212a. The gas discharge pipe 214a is provided with a flow rate adjusting valve 163 and a massflow meter (MFM) 173, which flow rate adjusting valve 163 and MFM 173 control the discharge rate of the sheath gas from the second classification section 20b. The gas supply pipe 212a is provided with a massflow controller 116a, which controls the supply flow rate of the sheath gas to the second classification section 20b.

For example, as illustrated in (a) of FIG. 4, in a case where the sheath gas flows from the upper part toward the lower part of the second classification section 20b, the DMA 400 is operated by use of just the gas supply pipe 212 and the gas discharge pipe 214 for supplying and discharging the sheath gas. On the other hand, as illustrated in (b) of FIG. 4, in a case where the sheath gas flows from the lower part toward the upper part of the second classification section 20b, the DMA 400 is operated by use of just the gas supply pipe 212a and the gas discharge pipe 214a for supplying and discharging the sheath gas.

(Main Characteristics of DMA 400)

The DMA 400 is a hybrid DMA of the DMA 100 described in Embodiment 1 and the DMA 300 described in Embodiment 2, and achieves the advantages of both the DMAs.

For example, (a) of FIG. 4 illustrates a state in which the outlet slit 106 is used, with the on-off valve 130 "closed" and the on-off valve 131 "opened". That is, the DMA 400 functions as a device equivalent to the DMA 100. Meanwhile, (b) of FIG. 4 illustrates a state in which the outlet slit 106a is used, with the on-off valve 130 "opened" and the on-off valve 131 "closed". That is, the DMA 400 functions as a device equivalent to the DMA 300.

Embodiment 4

Figure 5:
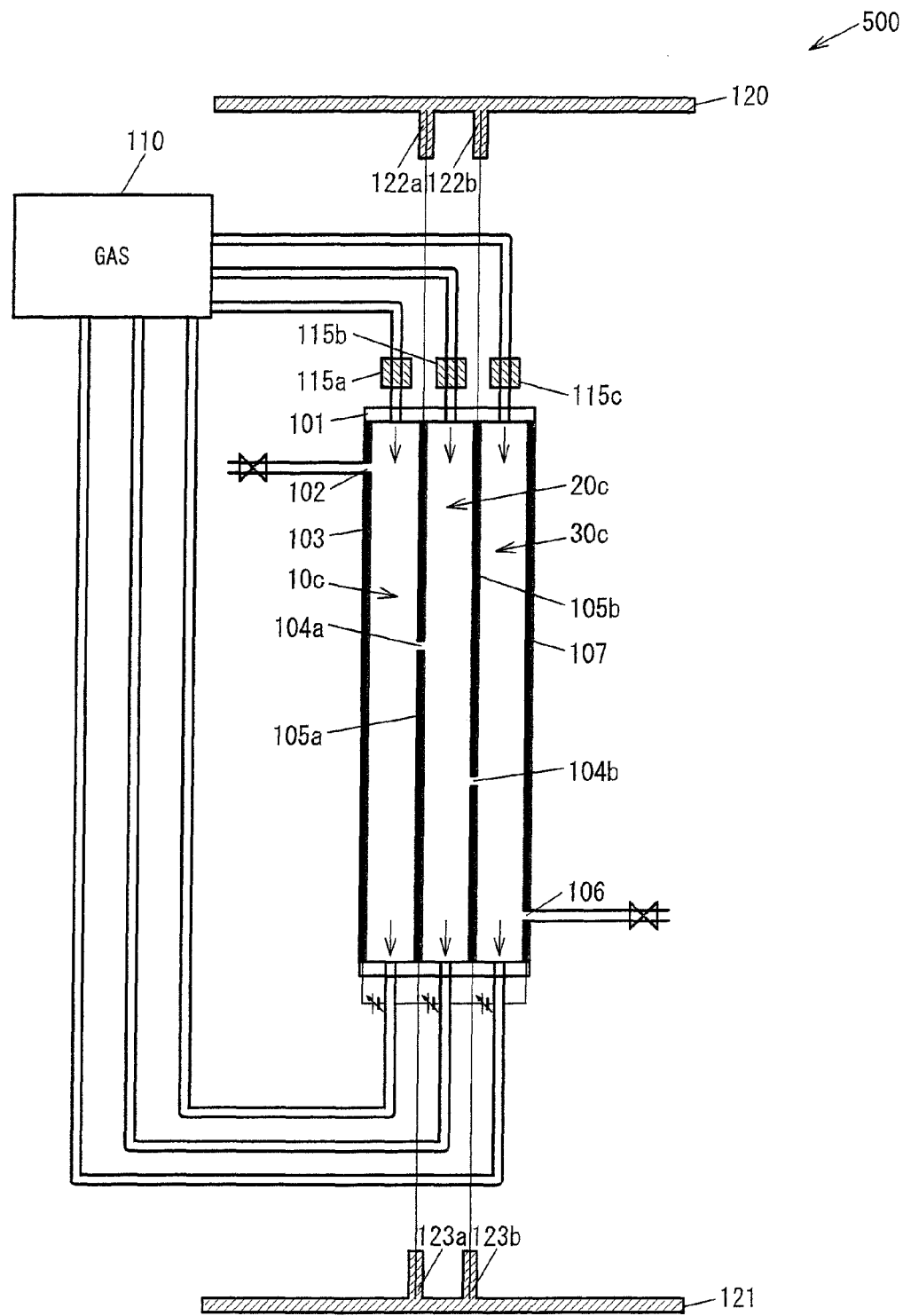
FIG. 5 is a cross-sectional view schematically illustrating a configuration of a DMA according to still another embodiment of the present invention.

The following describes still another embodiment of the DMA according to the present invention with reference to FIG. 5. FIG. 5 schematically illustrates a cross section of the DMA 500 taken along a plane perpendicular to the slits. For easy explanation, the components having the same functions as the components of the DMA 100 according to Embodiment 1 are denoted by the same reference signs and are not described. The present embodiment mainly describes differences from Embodiment 1.

(Configuration of DMA 500)

As illustrated in FIG. 5, the DMA 500 adds another classification section to the DMA 100. That is, in the DMA 500, the number of stages in the classification section is increased from two to three stages. With this configuration, the DMA 500 can perform an efficient multistage classification with a more improved gas removal capability compared to the DMA 100, additionally to achieving the advantages of the DMA 100.

The DMA 500 includes two intermediate electrodes 105a and 105b, in addition to the inlet electrode 103 having the inlet slit 102 and the outlet electrode 107 having the outlet slit 106. The intermediate electrodes 105a and 105b have slits 104a and 104b, respectively. Each of the inlet electrode 103, the intermediate electrodes 105a and 105b, and the outlet electrode 107 are fixed to the inner walls of the classification tank 101 at either side, thereby forming a sealed first classification section 10c, second classification section 20c, and third classification section 30c.

Each of the classification sections is connected to the sheath gas supply device 110 via a delivery pipe, at the sheath gas inlet provided on the top of the classification sections. The delivery pipes have massflow controllers 115a, 115b, and 115c, respectively. The flow rate of the sheath gas that flows in the classification sections are individually controllable depending on the opening and closing of the massflow controllers 115a, 115b, 115c as well as to what extent the massflow controllers 115a, 115b, and 115c are opened or closed.

In the DMA 500, a position adjusting mechanism 120 includes a guide rail 122a which extends to the intermediate electrode 105a in the vertical direction and a guide rail 122b which extends to the intermediate electrode 105b in the vertical direction, and a position adjusting mechanism 121 includes a guide rail 123a which extends to the intermediate electrode 105a in the vertical direction and a guide rail 123b which extends to the intermediate electrode 105b in the vertical direction. The intermediate electrodes 105a and 105b are continuously movable in an up-and-down direction (in the direction in which the sheath gas flows) along the guide rails, and are fixable at a desired position. In a case where the intermediate electrodes 105a and 105b are moved by a same distance in a same direction, it is possible to change just the classification lengths of the first classification section 10c and the classification lengths of the third classification section 30c, without changing the classification length of the second classification section 20c.

Each of the classification sections is connected to the sheath gas supply device 110 at the sheath gas outlet provided at the bottom of the classification section, via a delivery pipe. That is, the DMA 500 is configured such that the sheath gas which has passed through the classification sections is collected, filtered, and then reused. Note that the flow rate control mechanism provided following the sheath gas discharge is not depicted in FIG. 5.

Embodiment 5

Figure 6:
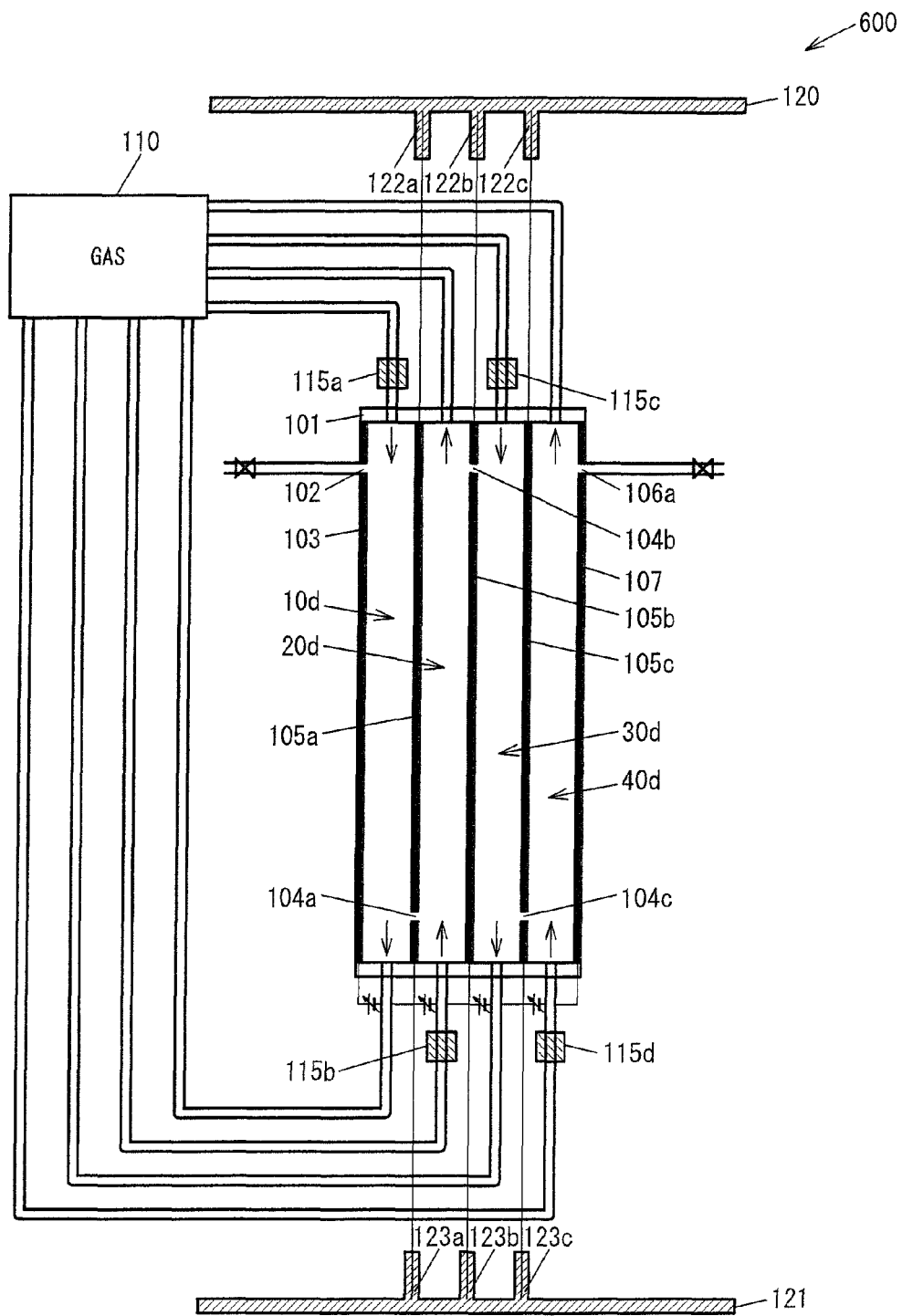
FIG. 6 is a cross-sectional view schematically illustrating a configuration of a DMA according to still another embodiment of the present invention.

The following describes still another embodiment of the DMA according to the present invention with reference to FIG. 6. FIG. 6 schematically illustrates a cross section of the DMA 600 taken along a plane perpendicular to the slits. For easy explanation, the components having identical functions as the components of the DMA 300 according to Embodiment 2 are denoted by the same reference signs and are not described. The present embodiment mainly describes differences from Embodiment 2.

(Configuration of DMA 600)

As illustrated in FIG. 6, the DMA 600 is configured by directly coupling two configurations each equivalent to the classification tank included in the symmetrical DMA 300, thereby having the number of the classification sections be increased from two to four. With this configuration, the DMA 600 can perform an efficient multistage classification with a more improved gas removal capability in comparison with the DMA 300, additionally to achieving the advantages of the DMA 300.

The DMA 600 includes three intermediate electrodes 105a, 105b, and 105c, in addition to the inlet electrode 103 having the inlet slit 102 and the outlet electrode 107 having the outlet slit 106a. The intermediate electrodes 105a, 105b, and 105c have slits 104a, 104b, and 104c, respectively. Each of the inlet electrode 103, intermediate electrodes 105a, 105b, and 105c, and outlet electrode 107 is fixed to the inner walls of the classification tank 101 at either side, thereby forming a sealed first classification section 10d, second classification section 20d, third classification section 30d, and fourth classification section 40d.

Each of the first classification section 10d and the third classification section 30d is connected with the sheath gas supply device 110 at the sheath gas inlet provided on the top of the classification sections, via a delivery pipe. Each of the second classification section 20d and the fourth classification section 40d is connected to the sheath gas supply device 110 at the sheath gas inlet provided at the bottom of the classification sections, via a delivery pipe. The delivery pipes have massflow controllers 115a, 115b, 115c, and 115d, respectively. The flow rate of the sheath gas that flows in the classification sections are individually controllable, in accordance with the opening and closing of the massflow controllers 115a, 115b, 115c, and 115d as well as to what extent each of the massflow controllers 115a, 115b, 115c, and 115d is opened or closed.

In the DMA 600, a position adjusting mechanism 120 includes a guide rail 122a which extends to the intermediate electrode 105a in the vertical direction, a guide rail 122b which extends to the intermediate electrode 105b in the vertical direction, and a guide rail 122c which extends to the intermediate electrode 105c in the vertical direction, and a position adjusting mechanism 121 includes a guide rail 123a which extends to the intermediate electrode 105a in the vertical direction, a guide rail 123b which extends to the intermediate electrode 105b in the vertical direction, and a guide rail 123c which extends to the intermediate electrode 105c in the vertical direction. The intermediate electrodes 105a, 105b, and 105c are continuously movable in an up-and-down direction (in the direction in which the sheath gas flows) along the guide rails, and are fixable at a desired position. For example, in a case where a combination of the intermediate electrodes 105a and 105c is moved by a same distance in the same direction, it is possible to optimize the upper limit of particle size of charged particles that can be classified. Meanwhile, in a case where a combination of the intermediate electrodes 105a and 105b or a combination of the intermediate electrodes 105b and 105c are moved by a same distance in the same direction, it is possible to change just the classification lengths of the first classification section 10d and the fourth classification section 40*d* without changing the classification length of the second classification section 20*d* or the third classification section 30*d*.

It is also possible to use part of the DMA 600 as necessary. For example, a particle discharge pipe (not illustrated) may be provided at the bottom of the third classification section 30*d* to discharge the charged particles that have a desired particle size, from the classification tank 101 so that the fourth classification section 40*d* is not used. In this case, the supply of the sheath gas into the fourth classification section 40*d* is not necessary.

As with the DMA 500 described in Embodiment 4, the DMA 600 is configured in such a manner that the sheath gas which has passed through the classification sections is collected, filtered, and then reused. Note that the flow rate control mechanism provided following the sheath gas discharge is not depicted in FIG. 6.

Embodiment 6

Figure 7:
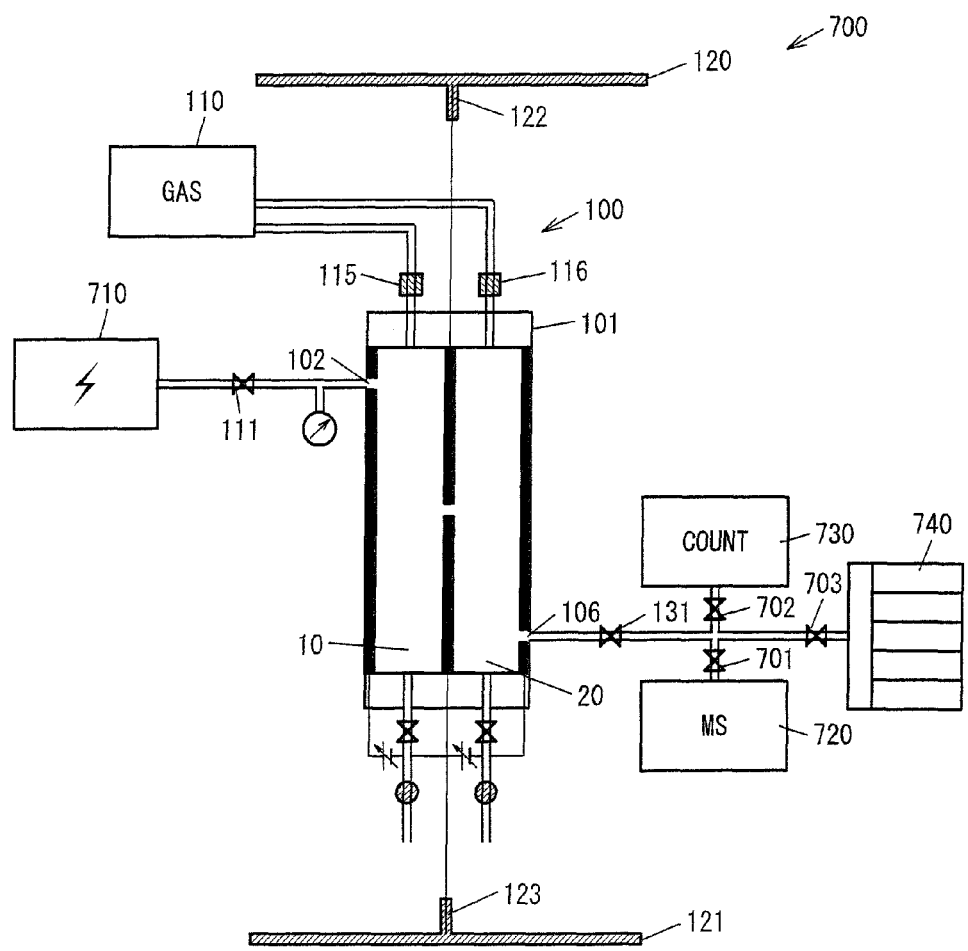
FIG. 7 is a schematic view illustrating a fine particle measuring and sorting system according to an embodiment of the present invention.

With reference to FIG. 7, the following describes a particle measuring and sorting system 700 according to the present invention. The particle measuring and sorting system 700 includes the DMA 100 (see Embodiment 1), a charging device 710, a mass spectrometer 720, a particle number counter 730, and a particle collection device 740.

The charging device 710 is connected to the inlet slit 102 of the DMA 100, via a delivery pipe. The mass spectrometer 720, the particle number counter 730, and the particle collection device 740 are all connected to the outlet slit 106 of the DMA 100 via a cross pipe.

Sample gas containing aerosol is charged by the charging device 710, whereby the sample gas becomes sample gas including charged aerosol. This sample gas is introduced into the classification tank 101 via the inlet slit 102 by opening the on-off valve 111, to be classified by the first classification section 10 and the second classification section 20. The charged aerosol having a predetermined size is discharged from the outlet slit 106.

In a case where mass spectrometry of the charged aerosol discharged from the outlet slit 106 is to be performed, the on-off valves 702 and 703 are closed and the on-off valves 131 and 701 are opened, to introduce the charged aerosol into the mass spectrometer 720. In a case where the number of particles in the charged aerosol discharged from the outlet slit 106 is to be counted, the on-off valves 701 and 703 are closed and the on-off valves 131 and 702 are opened, to introduce the charged aerosol into the particle number counter 730. Furthermore, by closing the on-off valves 701 and 702 and opening the on-off valves 131 and 703, it is possible to make the particle collection device 740 sort and collect the particles having a particular particle size.

As described in the above Embodiments 1 to 6, a DMA according to the present invention includes: (1) a classification tank including n (where n is an integer equal to or greater than 3) pieces of electrodes each having a planar shape, disposed in sequence in such a manner that the electrodes oppose each other as pairs each having a predetermined space provided therebetween, each of the n pieces of electrodes having at least one slit through which the charged particles pass; (2) a gas supply section supplying the classification tank with sheath gas; and (3) a voltage supply section applying a predetermined voltage between each of the pairs of the electrodes disposed opposing each other in the classification tank, the classification tank including (n−1) stages of classification sections for classifying the charged particles, each of the classification sections being formed by a respective one of the pairs of the electrodes disposed opposing each other, the gas supply section controlling a flow rate of the sheath gas supplied to the classification tank per classification section.

In Embodiments 1 to 6, DMAs including three to five planar electrodes have been described by way of example. However, the number of the planar electrodes is not particularly limited to three to five, and of course may be six or more. Further, in Embodiments 1 to 6, DMAs including rectangular (flat plate) electrodes as the planar electrodes are described as preferred examples. However, these are not the only possibilities. For example, a curved planar electrode can also be used. Specifically, the curved planar electrodes may be n (n is an integer equal to or greater than 3) pieces of cylindrical electrodes that are concentrically arranged.

In the DMA according to the present invention, the sheath gas may be flown into at least one pair of adjacent classification sections in such a manner that the sheath gas is flown into one classification section of the pair of adjacent classification sections in a direction opposite to that of the other classification section of the pair of adjacent classification sections. In this case, the DMA according to the present invention is configured in such a manner that the adjacent classification sections share one slit, and other slits (a slit on a particle inlet side of one classification section and a slit on a particle outlet side of the other classification section) are positioned both higher or both lower than the shared slit (see Embodiments 2 and 5).

In the DMAs described in Embodiments 1 to 6, the positions of the slits opened in the electrodes are changed by moving the planar electrode in an up-and-down direction with use of a position adjusting mechanism. However, how the positions of the slits are changed is not limited to this method. For example, the positions of the slits may be changed by configuring the DMAs so that it includes a plurality of planar electrodes that have slits opened therein at different positions, which plurality of planar electrodes are provided detachable from the DMA.

In the DMAs described in Embodiments 1 to 6, the supply flow rate of the sheath gas to the classification sections is automatically controlled by the massflow controllers while the discharge flow rate of the sheath gas is controlled manually. Meanwhile, it is also possible to configure the DMA in such a manner that the discharge flow rate of the sheath gas is also automatically controlled by a massflow controller or the like. Alternatively, the DMA according to the present invention may be configured so as to include one control section that automatically performs collective control of the supply flow rate and the discharge flow rate of the sheath gas in all the classification sections.

The particle size of the particles to be classified by the DMA according to the present invention is not particularly limited. However, it is especially preferable that the particle size of the fine particles be nanometer-scale to micrometer-scale.

As described above, a differential mobility analyzer (DMA) according to the present invention includes: a classification tank including n (where n is an integer equal to or greater than 3) pieces of electrodes each having a planar shape, disposed in sequence in such a manner that the electrodes oppose each other as pairs each having a predetermined space provided therebetween, each of the n pieces of electrodes having at least one slit through which the charged particles pass; a gas supply section supplying the classification tank with sheath gas; and a voltage supply section applying a predetermined voltage between each of the pairs of the electrodes disposed opposing each other in the classification tank, the classification tank including (n−1) stages of classification sections for classifying the charged particles, each of the classification sections being formed by a respective one of the pairs of the electrodes disposed opposing each other, the gas supply section controlling a flow rate of the sheath gas supplied to the classification tank per classification section.

In the DMA according to the present invention configured as above, the slits opened in the pair of electrodes disposed opposing each other in at least one of the classification sections are preferably variable in its relative position in a direction in which the sheath gas flows. For example, the DMA may include: a position changing mechanism changing the relative position of the slits in the pair of electrodes disposed opposing each other by relatively moving at least one of the opposing electrodes along the direction in which the sheath gas flows or along an opposite direction to the direction in which the sheath gas flows.

With the above configuration, it is possible to change the classification conditions relatively easily per classification section. In particular, it is not necessary to move other devices that are provided in a position following the DMA and that are provided in a position followed by the DMA if the positions of the slits are changed in the electrodes other than (i) the electrode provided with the inlet slit through which the charged particles are introduced into the classification tank and (ii) the electrode provided with the outlet slit from which the particles are discharged from the classification tank (i.e., in the intermediate electrodes positioned between the electrodes (i) and (ii)). Of course there is no need to provide the additional flow paths for connecting the DMA and the other devices. As such, it is not necessary to consider the effect of the diffusional deposition loss dependent on the particle diameter of the charged particles.

In the DMA according to the present invention configured as above, the sheath gas may be flown into at least one pair of adjacent classification sections in such a manner that the sheath gas is flown into one classification section of the pair of adjacent classification sections in a direction opposite to that of the other classification section of the pair of adjacent classification sections (symmetrical DMA). With this configuration, it is possible to secure greater classification length without increasing the length of the device. In consequence, it is possible to perform a multistage classification of the particles having a wider range of particle diameters, while maintaining the length of the device compact.

In the DMA according to the present invention configured as above, the voltage supply section may control the voltage to be applied per pair of the electrodes disposed opposing each other. This configuration makes it easier to change the classification conditions per classification section.

In the DMA according to the present invention configured as above, the n pieces of electrodes are preferably shaped as flat plates and are disposed parallel to each other in the classification tank. This makes it possible to provide a multistage classification DMA of parallel plate type.

In the DMA according to the present invention configured as above, the n pieces of electrodes include an electrode having a plurality of slits, the plurality of slits including a slit serving as a slit for discharging the charged particles outside the classification tank, the plurality of slits being opened at different heights of that electrode. This makes it possible to selectively use the slits for discharging the particles outside the classification tank depending on purposes. In addition, this makes it also possible to use the DMA both as a so-called symmetrical DMA and an asymmetrical DMA.

Further, in order to allow the slits to be selectively used, in the DMA according to the present invention, the gas supply section may control a direction in which the sheath gas flows, per classification section.

Moreover, in the DMA according to the present invention, the gas supply section preferably supplies the sheath gas to each of the classification sections at a substantially same flow rate as a discharge flow rate of the sheath gas discharged from the respective classification section.

EXAMPLE

The following describes an example of the present invention in more detail with use of an Example.

Example 1

The present Example manufactured a DMA 100 having the same configuration as the DMA 100 of Embodiment 1 (see FIG. 1). The DMA 100 was designed to have the following dimensions: L10=L20=25 (mm), a10=a20=5 (mm), and b10=b20=100 (mm). Using this DMA 100, a distribution of polystyrene latex (PSL) standard particles having an average particle diameter of 30 nm was measured under such a sheath gas flow rate condition that Qs10 and Qs20 were each independently 0 or 10 (std L/min). The results are shown together in FIG. 8. Note that the reference signs L10, L20, a10, a20, b10, b20, Qs10, and Qs20 are of those been described in Embodiment 1.

The PSL standard particles that were diffused in a solution were aerosolized in an electrospray ionization device, brought into the Boltzmann equilibrium charge distribution in a neutralizing device, and then introduced into the DMA 100 via a sample gas inlet of the DMA 100 (the inlet slit 102 illustrated in FIG. 1). Note that it was confirmed that the pressure in the DMA 100 is maintained at atmospheric pressure under the above-described flow rate condition and while the sample gas inlet and the classification gas outlet are closed (i.e., while the on-off valves 111 and 131 illustrated in FIG. 1 are closed). A condensation aerosol particle counter (CPC) was connected with the DMA following the classification gas outlet (downstream of the outlet slit 106 illustrated in FIG. 1). The sample gas was introduced into the DMA 100 at a flow rate of 1.5 (L/min), and classification gas was supplied to the CPC at the same flow rate to count the number of the classified aerosol particles.

Figure 8:
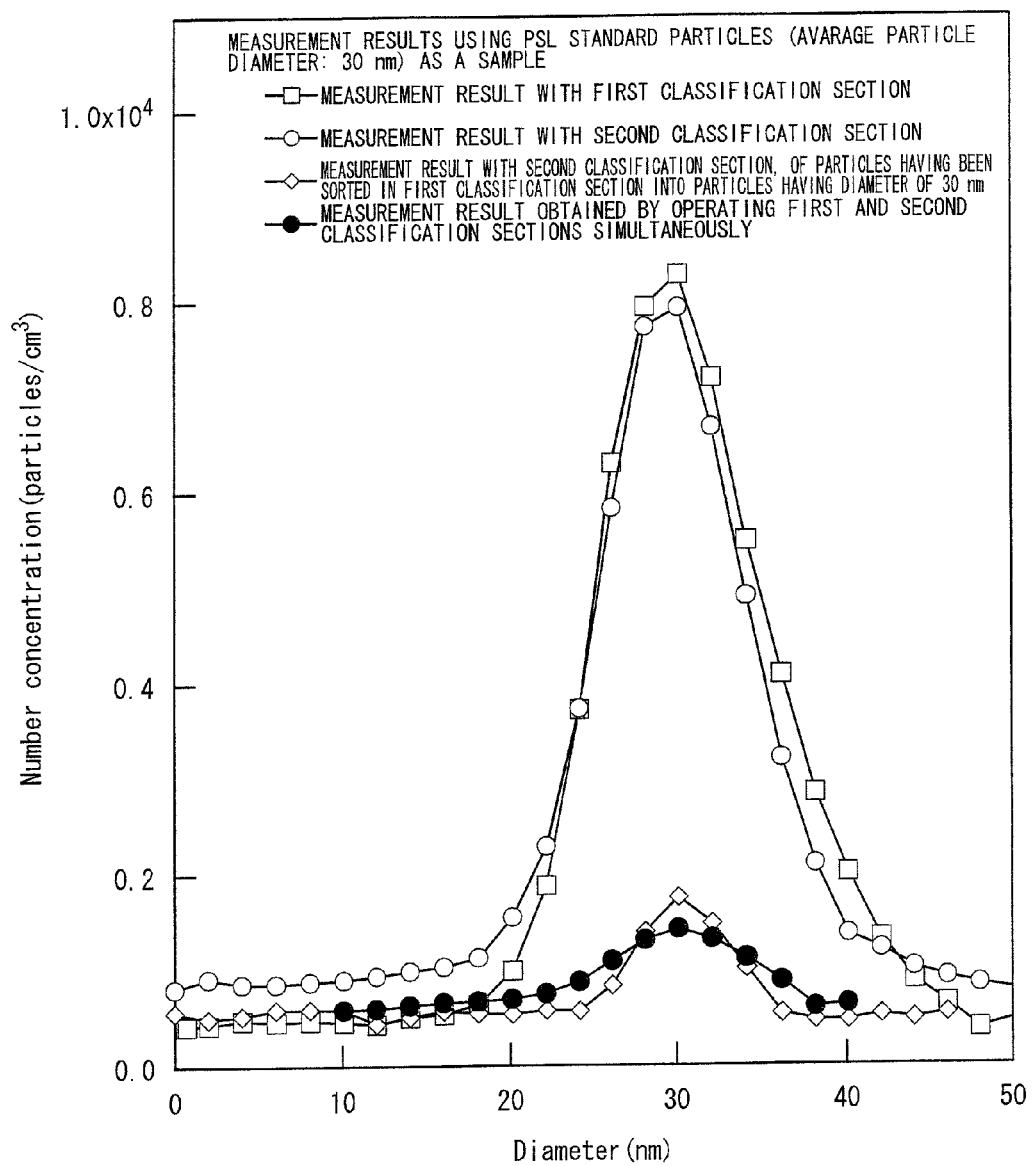
FIG. 8 is a graph showing an analysis result in an Example of the present invention.

A particle size distribution obtained by performing classification just with the first classification section 10 under a condition of Qs10=10 and Qs20=0 (std L/min) showed a substantially same particle size distribution peak as that obtained by performing the classification just with the second classification section 20 under a condition of Qs10=0 and Qs20=10 (std L/min), which peak was at 30 nm. This confirmed that each of the classification sections can properly classify standard particles. The results of these particle size distributions are shown in FIG. 8 by the outline boxes (results obtained with the first classification section) and the outline circles (results obtained with the second classification section).

Subsequently, particle size distribution was measured with the second classification section 20 under a condition of: Qs10=Qs20=10 (Std L/min); and a voltage applied to the first classification section 10 being fixed to a voltage that allows particles having a diameter of 30 nm to pass through. As a result of the aerosol particles being sorted in the first classification section 10 into the aerosol particles having the particle diameter of 30 nm, the particle diameter distribution showed a peak with a narrow distribution range. In consequence, it was confirmed that the first classification section 10 operated independently of and simultaneously with the second classification section 20, and that no change occurs to the particle size of the non-volatile PSL standard particles due to the classification. This result is shown in FIG. 8 by the outline rhombuses.

Next, particle size distribution of aerosol particles was obtained under the condition of Qs10=Qs20=10 (std L/min), and by operating the classification with the first classification section 10 and the second classification section 20 simultaneously, while the first classification section 10 and the second classification section 20 were applied a respective voltage that caused the aerosol particles classified in the first classification section 10 and that classified in the second classification section 20 to always have a same particle size. This particle size distribution showed a peak at 30 nm. As a consequence, it was confirmed that the DMA having two classification sections exhibits classification capability as one device. The result thereof is shown in FIG. 8 by the black circles.

INDUSTRIAL APPLICABILITY

The present invention is usable for a purpose of classifying and analyzing particles contained in gas.

REFERENCE SIGNS LIST

100, 300, 400, 500, 600 DMA (Differential Mobility Analyzer)
102 Inlet Slit (Slit)
104 Slit
106, 106a, 106b Outlet Slit (Slit)
103 Inlet Electrode (Plane Electrode)
105, 105a, 105b, 105c Intermediate Electrode (Electrode)
107, 107a, 107b Outlet Electrode (Electrode)
101 Classification Tank
108, 109 Voltage Generator (Voltage Supply Section)
10, 10c, 10d First Classification Section (Classification Section)
20, 20a, 20b, 20c, 20d Second Classification Section (Classification Section)
30c, 30d Third Classification Section (Classification Section)
40d Fourth Classification Section (Classification Section)
720 Mass Spectrometer (Particle Component Measuring Device)
700 Particle Counting and Sorting System (Particle Counting System, Particle Sorting System)
740 Particle Collection Device (Particle Sorting Device)

The invention claimed is:

1. A differential mobility analyzer classifying charged particles according to electrical mobility, the differential mobility analyzer comprising:
 a classification tank including n electrodes (where n is an integer equal to or greater than 3), each electrode having a planar shape, disposed in sequence in such a manner that the electrodes oppose each other as pairs, each pair having a predetermined space provided each of the electrodes, each of the n electrodes having at least one slit through which the charged particles pass;
 a gas supply section supplying the classification tank with sheath gas; and
 a voltage supply section applying a predetermined voltage between each of the pairs of the electrodes disposed opposing each other in the classification tank,
 wherein the classification tank includes (n−1) stages of classification sections for classifying the charged particles, each of the classification sections being formed by a respective one of the pairs of the electrodes disposed opposing each other, and each of the classification sections having a sheath-gas inlet,
 wherein the gas supply section controls a flow rate of the sheath gas supplied to the classification tank per classification section,
 wherein the gas supply section includes: (i) gas supply tubes connected to each respective sheath-gas inlet of the classification sections; and (ii) gas supply controlling means provided to each of the gas supply tubes, and
 wherein the sheath gas is flowed into at least one pair of adjacent classification sections in such a manner that the sheath gas is flowed into one classification section of the pair of adjacent classification sections in a direction opposite to that of the other classification section of the pair of adjacent classification sections.

2. A particle sorting system comprising:
 a differential mobility analyzer according to claim 1; and
 a particle sorting device sorting and collecting particles that have a predetermined particle size, the particles being classified by the differential mobility analyzer.

3. The differential mobility analyzer according to claim 1, wherein the gas supply means is a massflow controller.

4. The differential mobility analyzer according to claim 1, wherein the voltage supply section controls the voltage to be applied per pair of the electrodes disposed opposing each other.

5. The differential mobility analyzer according to claim 1, wherein the n of electrodes are shaped as flat plates and are disposed parallel to each other in the classification tank.

6. The differential mobility analyzer according to claim 1, wherein the gas supply section supplies the sheath gas to each of the classification sections at a substantially same flow rate as a discharge flow rate of the sheath gas discharged from the respective classification section.

7. A differential mobility analyzer classifying charged particles according to electrical mobility, the differential mobility analyzer comprising:
 a classification tank including n electrodes (where n is an integer equal to or greater than 3), each electrode having a planar shape, disposed in sequence in such a manner that the electrodes oppose each other as pairs, each pair having a predetermined space provided each of the electrodes, each of the n electrodes having at least one slit through which the charged particles pass;
 a gas supply section supplying the classification tank with sheath gas; and
 a voltage supply section applying a predetermined voltage between each of the pairs of the electrodes disposed opposing each other in the classification tank,
 wherein the classification tank includes (n−1) stages of classification sections for classifying the charged particles, each of the classification sections being formed by a respective one of the pairs of the electrodes disposed opposing each other, and each of the classification sections having a sheath-gas inlet,
 wherein the gas supply section controls a flow rate of the sheath gas supplied to the classification tank per classification section, and
 wherein the gas supply section includes: (i) gas supply tubes connected to each respective sheath-gas inlet of the classification sections; and (ii) gas supply controlling means provided to each of the gas supply tubes, wherein the n of electrodes include an electrode having a plurality of slits, the plurality of slits including a slit serving as a slit for discharging the charged particles outside the classification tank, and the plurality of slits being opened at different heights of that electrode, wherein the gas supply section controls a direction in which the sheath gas flows, per classification section, and wherein the gas supply section is capable of redirecting the direction, in which the sheath gas flows, to an opposite direction within at least one of the classification sections.

8. A particle measuring system comprising:
a differential mobility analyzer according to claim 7; and
a particle component measuring device analyzing chemical component of particles classified by the differential mobility analyzer.

9. A particle sorting system comprising:
a differential mobility analyzer according to claim 7; and
a particle sorting device sorting and collecting particles that have a predetermined particle size, the particles being classified by the differential mobility analyzer.

10. A differential mobility analyzer classifying charged particles according to electrical mobility, the differential mobility analyzer comprising:
a classification tank including n electrodes (where n is an integer equal to or greater than 3), each electrode having a planar shape, disposed in sequence in such a manner that the electrodes oppose each other as pairs, each pair having a predetermined space provided each of the electrodes, each of the n electrodes having at least one slit through which the charged particles pass;
a gas supply section supplying the classification tank with sheath gas; and
a voltage supply section applying a predetermined voltage between each of the pairs of the electrodes disposed opposing each other in the classification tank, wherein the classification tank includes (n−1) stages of classification sections for classifying the charged particles, each of the classification sections being formed by a respective one of the pairs of the electrodes disposed opposing each other, and each of the classification sections having a sheath-gas inlet, wherein the gas supply section controls a flow rate of the sheath gas supplied to the classification tank per classification section, and wherein the gas supply section includes: (i) gas supply tubes connected to each respective sheath-gas inlet of the classification sections; and (ii) gas supply controlling means provided to each of the gas supply tubes; and a position changing mechanism including a pair of guide rails for guiding continuous movement of one of the electrodes in a pair of the electrodes disposed opposing each other in the direction in which the sheath gas flows or the opposite direction in at least one of the classification sections, the position changing mechanism changing the relative position of the slits in the pair of electrodes disposed opposing each other by the continuous movement of the electrode.

11. A particle measuring system comprising:
a differential mobility analyzer according to claim 10; and
a particle component measuring device analyzing chemical component of particles classified by the differential mobility analyzer.

12. A particle sorting system comprising:
a differential mobility analyzer according to claim 10; and
a particle sorting device sorting and collecting particles that have a predetermined particle size, the particles being classified by the differential mobility analyzer.

13. A particle measuring system comprising:
a differential mobility analyzer according to claim 1; and
a particle component measuring device analyzing chemical component of particles classified by the differential mobility analyzer.

* * * * *